US008924234B2

(12) United States Patent
Renzi et al.

(10) Patent No.: US 8,924,234 B2
(45) Date of Patent: *Dec. 30, 2014

(54) STREAMING VIDEO NETWORK SYSTEM (71) Applicant: Image Stream Medical, Inc., Littleton, MA (US)

(72) Inventors: Peter Renzi, Acton, MA (US); Eddie E. Mitchell, Harvard, MA (US)

(73) Assignee: Image Stream Medical, Inc., Littleton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/840,293

(22) Filed: Mar. 15, 2013

(65) Prior Publication Data

US 2013/0201273 A1 Aug. 8, 2013

Related U.S. Application Data (63) Continuation of application No. 11/510,337, filed on Aug. 24, 2006, now Pat. No. 8,401,869.

(60) Provisional application No. 60/710,886, filed on Aug. 24, 2005.

(51) Int. Cl.
G06Q 50/00 (2012.01)
(52) U.S. Cl.
USPC .................................. 705/2; 705/3
(58) Field of Classification Search
CPC ..... G06Q 50/22; G06Q 50/24; G06F 19/3418
USPC ........................................ 705/2, 3
See application file for complete search history.

(56) References Cited

U.S. PATENT DOCUMENTS

| 6,049,823 | A  | 4/2000  | Hwang           |
|-----------|----|---------|-----------------|
| 6,602,185 | B1 | 8/2003  | Uchikubo et al. |
| 7,092,376 | B2 | 8/2006  | Schuman         |
| 7,343,618 | B2 | 3/2008  | Sakamoto et al. |
| 2002/0138842 | A1 | 9/2002 | Chong et al.   |
| 2003/0188318 | A1 | 10/2003 | Liew et al.    |
| 2004/0172652 | A1 | 9/2004 | Fisk et al.    |
| 2005/0060211 | A1 | 3/2005 | Xiao et al.    |
| 2005/0166239 | A1 | 7/2005 | Uchikubo et al. |

FOREIGN PATENT DOCUMENTS

EP 1755308 A2 3/2003

*Primary Examiner* — Elaine Gort
*Assistant Examiner* — Jonathan K Ng
(74) *Attorney, Agent, or Firm* — Loginov & Associates, PLLC; William A. Loginov (57) ABSTRACT A distributed, digital, network-based, streaming video allows users to view live streaming digital video from multiple video sources in operating rooms at any location connected to a network. One or more video sources in an operating room are connected to a streaming video encoder capable of converting the video to a network packet stream. Once the digital video stream is available on the network, it may be accessed and routed through the use of a streaming video control server. The streaming video control server is responsible for user authentication and access for remote viewing and video source selection. The control server also provides audit logging services, operating room selection and overall system resource allocation. The video control server also provides a network-based remote control interface, which enables other systems to communicate on the streaming video network, and allows for remote control of visualization from an integrated operating room control system.

22 Claims, 6 Drawing Sheets

FIG. 8

STREAMING VIDEO NETWORK SYSTEM

RELATED APPLICATIONS

This application is a continuation of co-pending U.S. patent application Ser. No. 11/510,337, by Renzi et al., filed Aug. 24, 2006, entitled STREAMING VIDEO NETWORK SYSTEM, the entire disclosure of which is herein incorporated by reference, which claims the benefit of U.S. Provisional Patent Application Ser. No. 60/710,886, by Renzi et al., filed Aug. 24, 2005, entitled Streaming video network system, the entire disclosure of which is herein incorporated by reference.

FIELD OF THE INVENTION

The invention relates generally to the streaming of digital video and audio over data networks, where the source originates from medical clinical or surgical procedures, where remote visualization is required from other locations, such as operating rooms, offices or conference rooms, where remote selection and control of video sources may be required, and where HIPAA compliance enabling features are needed.

BACKGROUND OF THE INVENTION

With the development and practice of Minimally Invasive Surgical (MIS) technique, has come a proliferation of medical and non-medical devices that generate video in the hospital operating room and in medical clinics. The term MIS is used to describe a number of surgeries as well as diagnostic procedures. MIS includes both laparoscopy (surgery through small holes) and endoscopy (diagnostic and therapeutic procedures performed through the body's organs and vessels). In traditional surgeries, a surgeon needs to make a large incision in order to operate. With MIS, the surgeon makes a few small holes—usually less than ½ an inch. The surgeon then inserts specially designed, thin instruments and sophisticated video equipment to perform the operation through the smaller opening. The small incisions required for MIS generate less pain, reduces hospital stays, cause less scarring and facilitate rapid recovery. A common element of MIS procedures is that a video camera and a monitor is required for the surgeon to visualize the operative field. By using video-assisted equipment, the surgeon has better visualization and magnification of internal organs and structure. Since the operative field monitor can be seen by support staff inside the operating room, awareness of the surgical procedure is improved and the staff is better able to support the surgeon. Several other sources of video have recently emerged in the operating room including cameras attached to surgical microscopes, cameras mounted inside surgical lights and pan/zoom/tilt cameras mounted to walls inside the operating room.

Integrated Operating Room (IOR) technology has been developed and visualization tools are emerging and evolving to assist medical professionals with the management of this video and equipment within the operating room. Given that current art video cameras for the operating room environment output an analog signal, that these cameras typically are used for several years, and that analog video connections such as s-video and composite are well known and understood in the art, IOR technology inside the operating room routes analog video signals exclusively with rare exception.

Outside the operating room, a need has emerged for viewing live video from cameras located inside the operating room. Physicians who are scheduled to perform a procedure in an operating room will often want to check on the readiness of the staff and the patient prior to walking into the operating room theatre. With remote viewing capability, the physician has the ability to confirm 'first hand' the readiness of the staff and patient. Furthermore, a peer, fellow or resident may desire or require assistance with a procedure, Again, the physician is not required to enter the operating room, or operating theater, thus reducing the need to travel to the operating room, dress in scrubs, and sometimes scrub into a procedure. Another example of this need involves intra-procedure consultation between operating rooms in which a surgeon requests a second opinion from peer surgeons located in other operating rooms within the preoperative services department. This type of consultation requires that an on-demand video conference be established between operating rooms in which both video and audio can be shared. Yet another example of this need involves real-time collaboration between pathology and the operating room in which the surgeon can show the pathologist video indicating from where a cancer biopsy was taken. The area of staff and student training is another area that benefits significantly from the ability to view high-quality live-video outside the operating room. Students and additional staff do not need to be present in the operating room, causing crowding, and potential distractions for the surgeon. Rather, they can be at a conference room location, or distributed at a variety of locations across the hospital campus.

Another example of this need is for nurse management to have visibility into operating room so that scheduling and resource management may be facilitated. An additional element of this need is that the nurse management would like to have visibility into several rooms simultaneously. The ability to remotely observe operating rooms has been shown to improve staff scheduling, room turnover and room cleaning times. Access to this type of remote visualization toolset has the potential to improve efficiency and save time for both physician and non-physician caregivers.

Consistent with the type of technology used for IOR solutions, current art systems view video outside the operating room through the use of analog video cable infrastructure. Although the video quality of analog systems is generally adequate for current art cameras, this approach has several key limitations:

The number of users served by this solution is limited, because hard-wired video signals must be brought to each 'user'

The number of locations that can be served by this solution is equally so limited.

Wide-scale deployment of this solution is severely limited in all but new construction, due to the extensive cable infrastructure that must be installed.

Dedicated viewing hardware, analog switching equipment and displays are often required in order to complete the solution.

Distance limitations exist for video that must be addressed by expensive fiber-optic transmission equipment.

Usage and viewing of this video is extremely difficult, if not impossible to track.

The solution is not easily scalable to add more locations or more sources at a given location.

The cost of installing and maintaining the dedicated video cable infrastructure is high.

It is also important to note that the ability to remotely view a single video source of video from inside the operating room is generally inadequate. Depending on the type of operation being performed and the number of surgical modalities being employed, the remote viewer may need to see video from multiple sources such as the OR room camera, surgical light camera, microscopic camera or the endoscopic camera.

Accordingly, the remote viewer requires the ability to switch remotely between the source video modalities until the proper view is selected.

As digital video compression and video streaming technologies have developed, they have become capable of offering high-quality video with low-bandwidth consumption on Ethernet data networks. This has made the technology a viable and useful alternative to the hard-wired approaches, while offering substantially more flexibility. Some examples include:

A virtually limitless number of users and locations can be simultaneously served.

Dedicated viewing stations are not required.

Viewing can be accomplished on any standard 'Windows' computer with the proper configuration and network connectivity.

Viewing is also possible on non Windows platforms, such as Apple MAC using open source applications.

Digital streaming video can be viewed anywhere in the hospital, on the hospital campus, or via wide area broadband connections off the hospital campus.

Smart digital video walls can be constructed and fed by embedded video decoding hardware.

Users may take advantage of the ability to remotely control certain devices, such as Pan/Zoom/Tilt (PZT) cameras.

Users may take advantage of the ability to select and view video from a multitude of devices in the operating room via remote selection capabilities.

Authorization and authentication controls, audit trails, and auto-logoff functions can be employed, to protect and track access to live content.

Content can be accessed over standard Ethernet networks, with firewall and VPN encryption capabilities.

The systems and methods described herein are unique relative to the traditional broadcast service offerings, in that this solution becomes part of the hospital's infrastructure and does not require a staff of professionals to operate. As such, it is effectively owned and operated by the staff, and does not require extensive training to use. Depending on local network policy, the system may be configured for one-to-one (unicast) or one-to-many (multicast) transmissions. Being part of the hospital operating room infrastructure, the system is always ready and available for use.

Accordingly, there is a need in the art for a system that affords surgeons and medical professionals remote access to live video generated in hospital operating rooms and clinics. Such system should offer flexibility in the format, transport medium, and viewing location of the digital video streams. The system must also offer security and auditing capabilities.

SUMMARY OF THE INVENTION

It is an objective of the invention to improve operating room, staff and surgeon efficiency by providing live remote access to video which originates in hospital operating rooms and clinics. It is a further object of the present invention to increase the level of control that users can leverage over the video sources at the originating location. It is an added object of the invention to increase the potential audience and number of locations from which live-video can be accessed, such as operating rooms, offices, conference rooms and video walls to name a few. It is also an object of the current invention to offer an adequate level of auditing and security controls to assist hospitals in their need to be HIPAA compliant.

The present invention achieves these and other objectives by providing a distributed, digital, network-based, streaming video solution that allows users to view live operating room video from virtually any location that is connected to a network. One or more video sources in an operating room may be connected to a device (streaming video encoder) capable of converting the video to a network packet stream. Once the digital video stream is available on the network, it may be accessed and routed through the use of a streaming video control server. The streaming video control server is responsible for user authentication and authorization and web page access for remote viewing and video source selection by users. The control server also provides audit logging services, operating room selection and overall system resource allocation. The video control server also provides a network-based remote control interface, which enables other systems to communicate on the streaming video network. This allows for remote control of visualization from an integrated operating room control system (for example: Crestron or AMX) and provides the ability for one operating room to look into other operating rooms.

In accordance with one general aspect of the invention, a user interface is provided that is accessible via standard web-browser technology from a personal computer. This embodiment includes a familiar, user-friendly interface to provide access to the desired services. To begin a viewing session, the user opens a browser, and navigates to the appropriate URL (such as http://imagestream/lsp), and is presented with a login page. To gain access to the system, the user must enter their username and password. Once the user has been authenticated, they are granted access to the list of available operating rooms with specialties that match those of the user. The user is then able to select from any of the available operating rooms for live viewing. Once the link for the desired operating room has been selected, the viewing and control page is presented. A sample viewing page is presented below.

The user is presented with a live video view of the operating room, or some alternate view, as shown in the center of the screen sample. The user is optionally provided with video device selection buttons (left) which allow selection of alternate video sources that are located within the operating room. Advanced users may be granted control over certain controllable OR cameras, such as Pan/Zoom/Tilt or Surgical Light Cameras. When the operating room is selected, a programmable session timer is activated, which will automatically log the user out of the session, once the time expires. Five minutes prior to the expiration of the viewing session, users are allowed to extend their viewing session.

Administrative services are provided for the purpose of system setup, as well as system usage monitoring, user setup, room privacy controls, and system diagnostics.

In accordance with another aspect of the present invention, there is provided a streaming digital video control server (4), which incorporates a network control linkage to a video switching system (2) located in or near the operating room. To the switching system (2) may be connected a multitude of surgical and non-surgical video devices (1) in a video operating room. In this configuration, one or more video streaming devices (3) (where a video streaming device converts video to packet-based network digital video stream) may be connected to the output of the video switching system and to the hospital data network (5). Users may access the streaming server and managed video streams from office PCs (7) or from other remote locations. All devices are registered with the streaming video control server, which has been designed to control video streams from a multitude of video streaming devices and formats.

And in another aspect of the invention, there is provided a system for streaming digital video over a data network, where the user has the ability to remotely control selected devices in the operating room. Devices of this category include, but are not limited to PZT cameras, as well as cameras embedded in surgical lights. While the user is viewing live video from one of these devices, they may control certain functions of the device.

Another aspect of the invention allows for the use of streaming video decoder devices, which are capable of receiving digital video streams and converting them to the original analog video or displayable digital signal format. Current art integrated operating systems typically utilize analog video switching systems, and therefore, these decoder devices are required to allow virtual video circuit connections to be established between operating rooms, or between operating rooms and conference rooms (as examples). The system allows for the creation of digital connections, but is dependent on available technology and operating room capabilities. The system architecture is flexible and will accommodate both analog and digital devices. Using analog and digital streaming video decoder technology within this aspect of the invention allows for the creation of a video wall, which can be used to simultaneously monitor all operating room locations.

A further aspect of the invention enables the transmission of pathology images onto the digital streaming network. Pathology images can be received and viewed at any of the locations serviced by the digital streaming network. Most importantly, pathology images can be viewed from within an operating room, saving valuable time that would be required to walk to and from pathology, and avoiding the sterility problem of surgeons having to exit and re-enter the sterile field.

In another aspect of the current invention, state and status metadata information is captured from the source operating room simultaneously with the video. The metadata is conveyed using one of several techniques so that users may view the information in conjunction with the video at the viewing location. Examples include the ability to combine operating room state information with video being displayed on a video wall. Another example includes the ability to collect and transmit patient vital signs information, which is overlaid onto the video as it is being viewed.

These and other aspects of the invention are herein described in detail, with reference to certain preferred and alternate embodiments which are illustrative but not exclusive of various ways in which the principles and concepts of the invention can be embodied and practiced.

BRIEF DESCRIPTION OF THE DRAWINGS

The foregoing and other features and advantages of the present invention will become apparent to those skilled in the art to which the present invention relates upon reading the following description with reference to the accompanying drawings, in FIG. 1 is a schematic diagram of an analog video distribution 'hub' which is commonly used by vendors in the medical/surgical video integration business.

DETAILED DESCRIPTION

Figure 1:
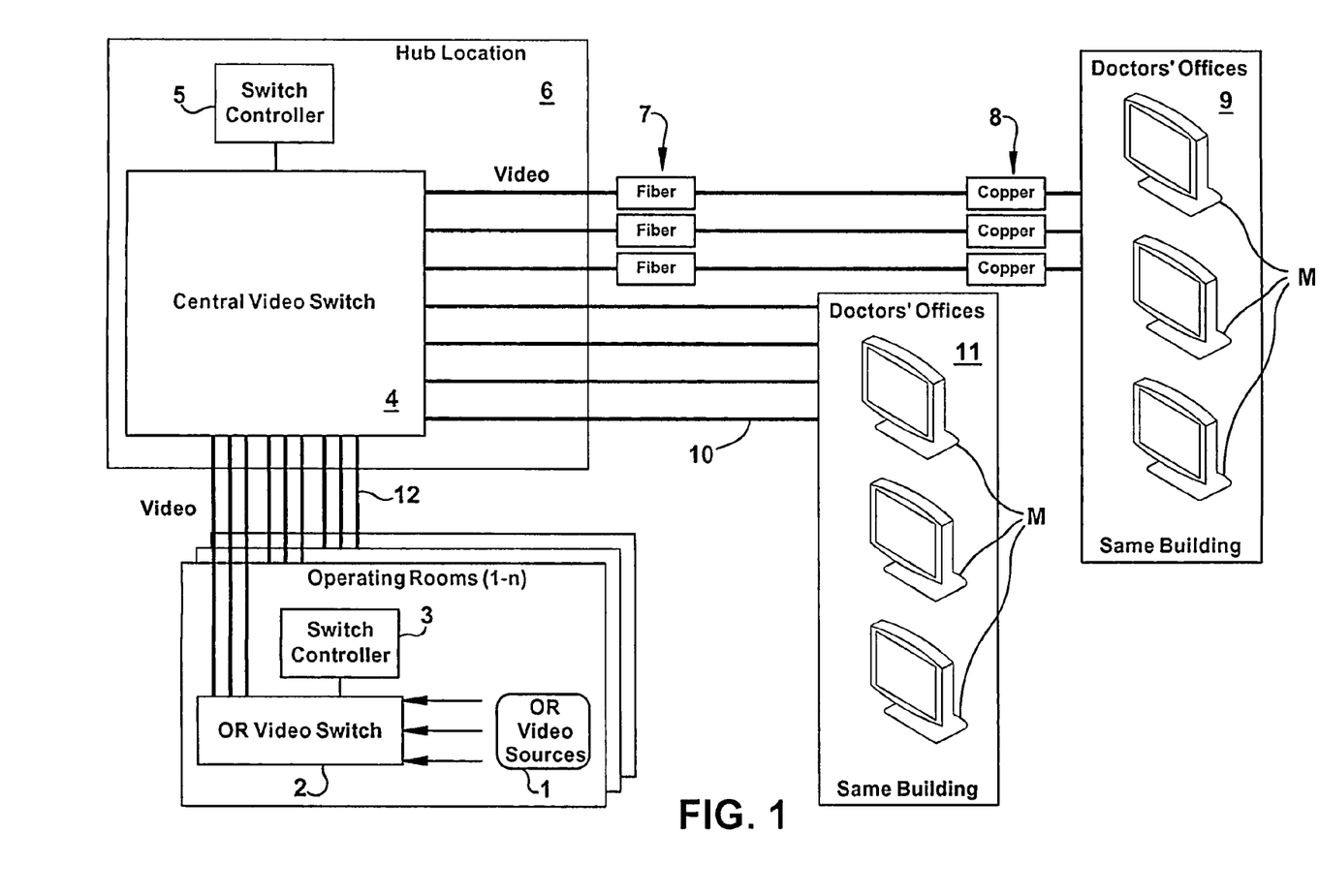

FIG. 1 is a schematic diagram of an analog video distribution system (hub) which enables OR to OR and Limited OR to Office visualization. Operating room video sources (1) may be connected to a video switch (2) located in or near the operating room. The video switch is controlled by a video switch controller (3). Video may alternatively be connected directly to the outbound video links 12, which are typically coaxial video cable linked back to a central hub location (6), and connected to a central video switch (4). The central video switch is controlled by a video switch controller (5). Video cabling, again typically coaxial cable (10), is run from the hub location (6) to viewing locations such as doctor's offices in the same building (11). For longer distances, fiber/copper transceivers (7, 8) are required, along with fiber infrastructure, in order for users in other buildings to view OR video. Dedicated monitors M at the remote viewing locations are used to visualize the video. Remote switching control is possible if the user is provided with a more advanced control system at the remote viewing location.

Figure 2:
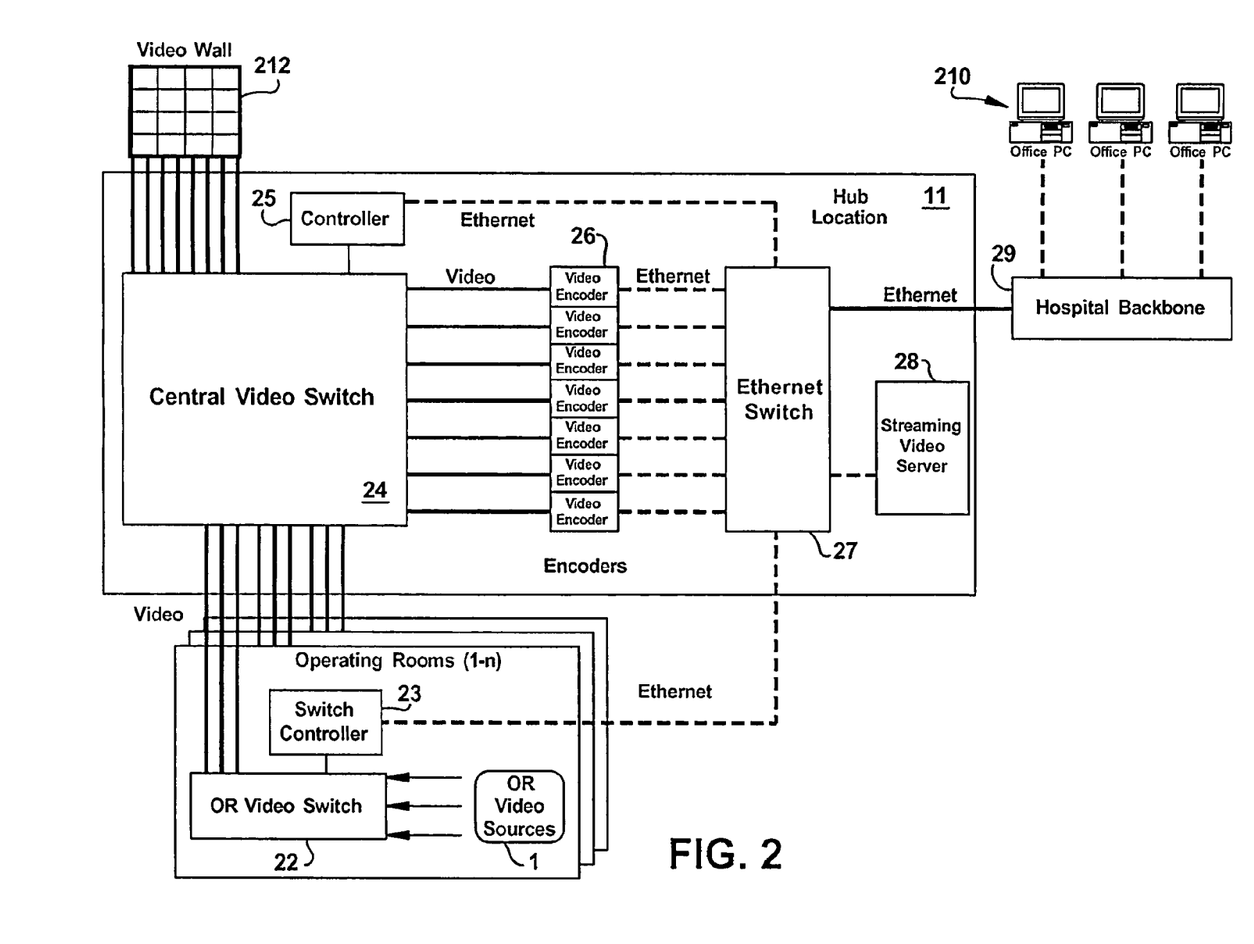
FIG. 2 is a schematic diagram of a mixed analog/digital video distribution 'hub' which was developed as a prototype iteration of the invention.

FIG. 2 is a schematic diagram of a mixed analog/digital video distribution network system which has similar capabilities and limitations of the system described with reference to FIG. 1, with the advantages of digital video streaming from a hub location, as further described. Multiple operating room video sources (1) are connected to a video switching system (22), under direct or indirect control of a control system (23). Outputs from the video switch (22) are linked to a central video switch (24), under direct or indirect control of a video control system (25). Video outputs from the central video switch (24) are connected to a bank (1 or more) of streaming video devices (26) (video encoders). It is the job of each streaming video device to convert the incoming video into a stream of digital video packets, and output those packets onto a standards-based Ethernet network and ultimately through an Ethernet switch (27). Once the video has been made available on the Ethernet it may be accessed via appropriately configured office computers (210), via the hospital network backbone (29). The streaming video control server (28) is responsible for orchestrating a multitude of operations in order to allow the viewing process to take place. A video wall (212) may be fed directly from the central video switch (24).

Users access video from this configuration using an office PC (210) through the use of a standard web browser. When the user first accesses the services of the streaming digital video network system, they are presented with a series of web pages, which are served from the streaming video web server (28).

This embodiment provides user access at virtually unlimited locations to view streaming video. The system requires analog video cabling between operating rooms and the hub location. This approach may be a relatively expensive solution for remote OR visualization due to the cost of the dedicated video infrastructure required.

Figure 3:
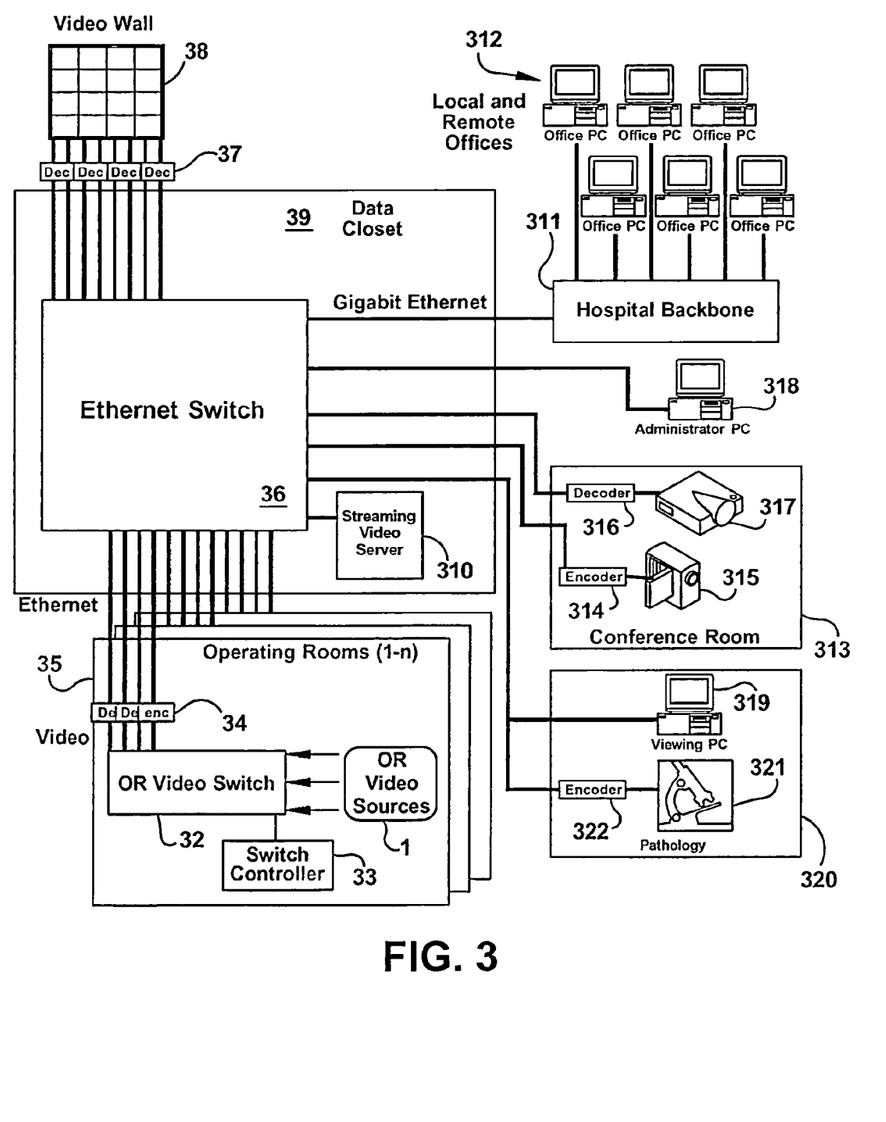
FIG. 3 is a schematic diagram that demonstrates many aspects of the current invention as a complete digital streaming infrastructure system used for linking video/audio from operating rooms to multiple other locations, virtually without limit.

FIG. 3 is a schematic diagram of streaming digital video system that demonstrates many aspects of the current invention in the form of a complete digital streaming infrastructure system used for linking video/audio from operating rooms to multiple other locations, virtually without limit. In this embodiment, video sources (1) within the operating room may be connected to a video switching device or system (32) under control of a switch controller (33). Output from the switching device is routed to one or more IP streaming video devices (34), which in turn, are connected by a standard data network (Ethernet or similar) to a network switch (36), typically located in a data closet (39). The streaming digital video control server (310) orchestrates access to the entire collection of devices which comprises the solution. For PC based users (312) residing in local and remote locations, the web-browser interface is used for visualizing operating room video over the hospital backbone (311).

Users in the operating room will use the integrated control system (switch controller) control interface (typically a touch panel) to access video from remote operating rooms. Video decoders (35) are located in proximity and connected to the video matrix switch (32) located in each operating room. This enables video from one operating room to be displayed in another. This further enables the remote video to be routed by the video switching system (32) to displays in the local operating room.

With this embodiment, video decoders (37) are used in conjunction with a video wall (38), which enables staff to simultaneously visualize video from all operating rooms. Because the content is digital, the video decoders can be controlled to show the current state of an operating room (i.e., privacy mode enabled, using microscope, etc).

An additional configuration of the invention allows the use of remote video encoders and decoders at locations such as conference rooms (313). In this configuration, video from a camera (315) is encoded onto the network (314) and made available for remote visualization anywhere on the network. In addition, a video decoder (316) consumes digital video streams from the network, and converts them into a displayable format, suitable for display on a monitor or projector (317).

A system administrator (318) is fully capable of configuring the system to support these modes of operation, and may dynamically establish bidirectional video/audio sessions between locations, such as an OR and a conference room.

Other locations, such as pathology (320) can be incorporated into the digital streaming network, by outfitting one or more microscopes (321) with a video camera and streaming video encoder (322) device. The video encoder, as usual, is connected to the hospital's Ethernet data network. Just as with other viewers of the system, Pathologists may use a standard PC to access and view the digital streaming video network. The pathology connection enables a physician to directly view what the pathologist sees in the microscope eliminating the need for the physician to go to pathology, or for a runner to bring photographs to surgery. Furthermore, the pathologist may directly view the surgical field where the specimen was extracted.

Figure 4:
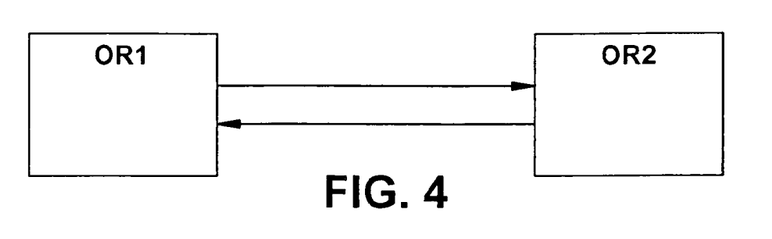
FIG. 4 is a logical operating room to operating room connection diagram.
Figure 5:
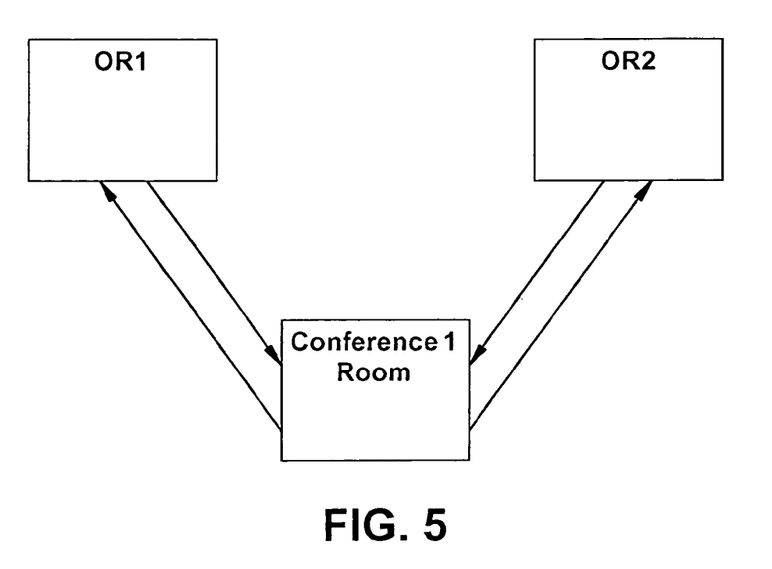
FIG. 5 is a logical OR to OR to Conference connection diagram.

FIGS. 4 and 5 illustrate a sampling of possible connection and communication scenarios presented as logical block diagrams. These are not exhaustive, but presented for the purpose of clarification and explanation of the system designs. FIG. 4 shows the logical bi-directional connection and information flow between two operating rooms, OR 1, OR2.

In one scenario, a user in OR1 may simply view video/audio from OR2. In more complex configurations, users may communicate over the bi-directional link using video and audio. The current invention fully supports these capabilities.

FIG. 5 shows the logical bi-directional connection and information flow between a conference room and one or more operating rooms. In this scenario, a single operating room may establish a connection with a conference or control room. The sequence may also be initiated from the conference or control room. In all cases, a unidirectional or bidirectional audio/video link may be established between the two locations. A user at a location may also request view-only services.

Figure 6:
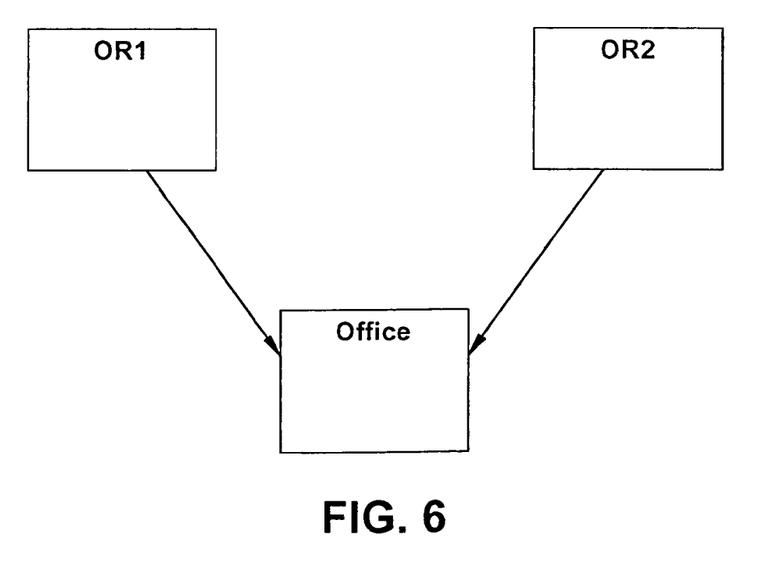
FIG. 6 is a logical OR/Office connection diagram.

FIG. 6 represents connectivity of a user in an office viewing video from 1 or more operating rooms. In this configuration, information flows from each OR (OR1, OR2) to the office viewing location.

Figure 7:
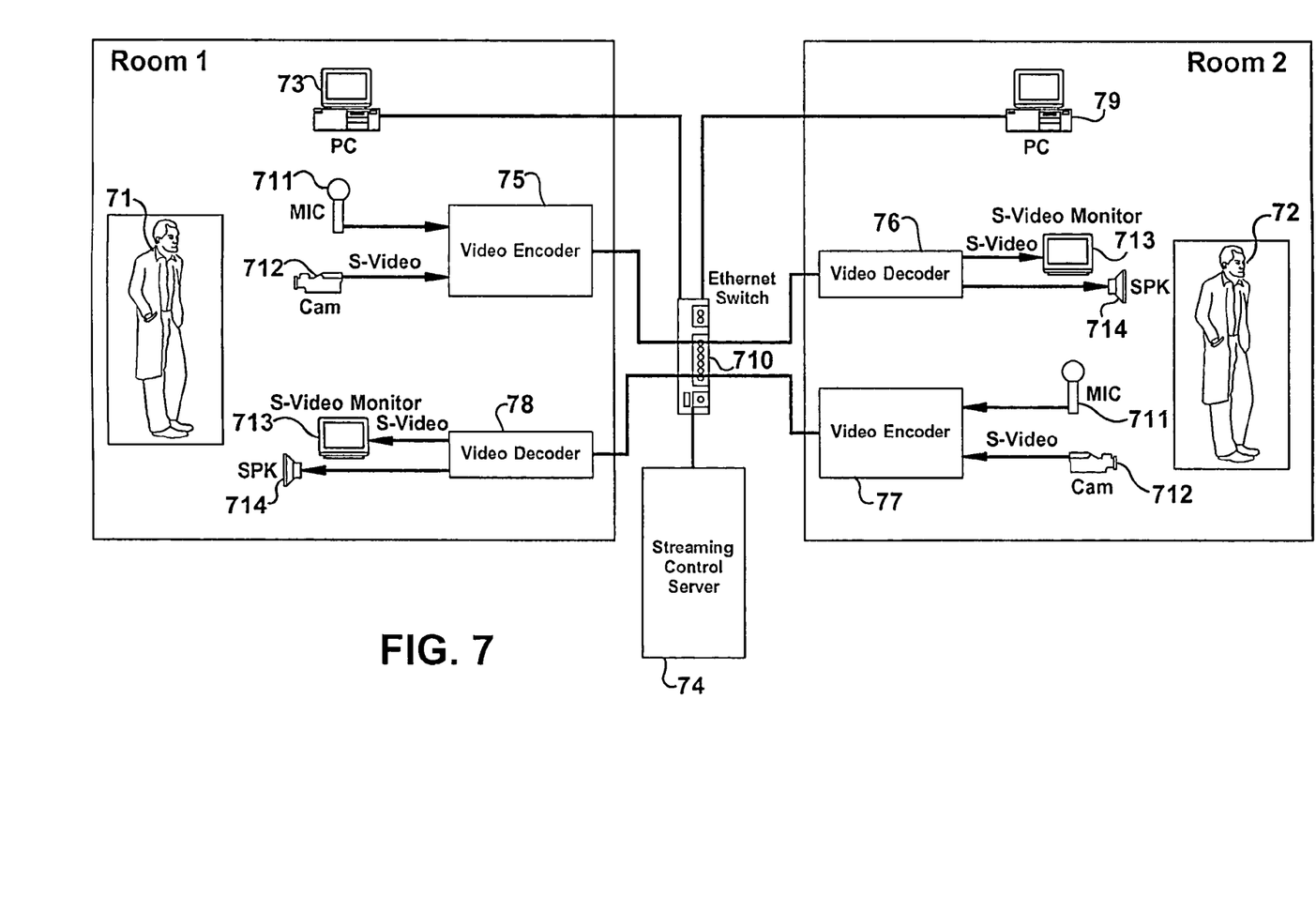
FIG. 7 is a diagram which describes one point-to-point video/audio communication scenario.

As shown in FIG. 7, if a user 71 in Room 1 (office, operating room, conference room, etc) wishes to contact a user 72 in Room 2 (office, operating room, conference room, etc), then user 71 initiates a connection to Room 2 by accessing a web session on a PC 73. User 71 selects the target room (Room 2 in this case) via the web interface, which is hosted on the Streaming Control Server 74 via Ethernet switch 710. The application software running on the server 74 initiates the following sequence of events:

1. A message is sent to the Video Decoder 76 in room 2.
2. The Video Decoder 76 is set to select and decode the video and/or audio stream from the Video Encoder 75 in room 1, as acquired from one or more cameras 712 or microphones 711.
3. A message is sent to the Video Decoder 78 in room 1.
4. The Video Decoder 78 is set to select and decode the video stream from the Video Encoder 77 in room 2, as acquired from one or more cameras 712 or microphones 711.

A point-to-point, bi-directional audio/video communication channel has been established once this sequence is completed. The Streaming control server 74 tracks the usage of the resources for the session, and frees them either based on an automatic timeout, or when the user logs off from the session.

The power of combined video and audio as communication mediums in a hospital environment is well understood. In the hospital environment, there are many other types and forms of information that can be collected and delivered in conjunction with the video to the viewing points throughout this digital infrastructure. Along with the live video, users of the system have expressed a strong desire to view other categories of information, such as room state, patient status, and staff present in the OR.

Figure 8:
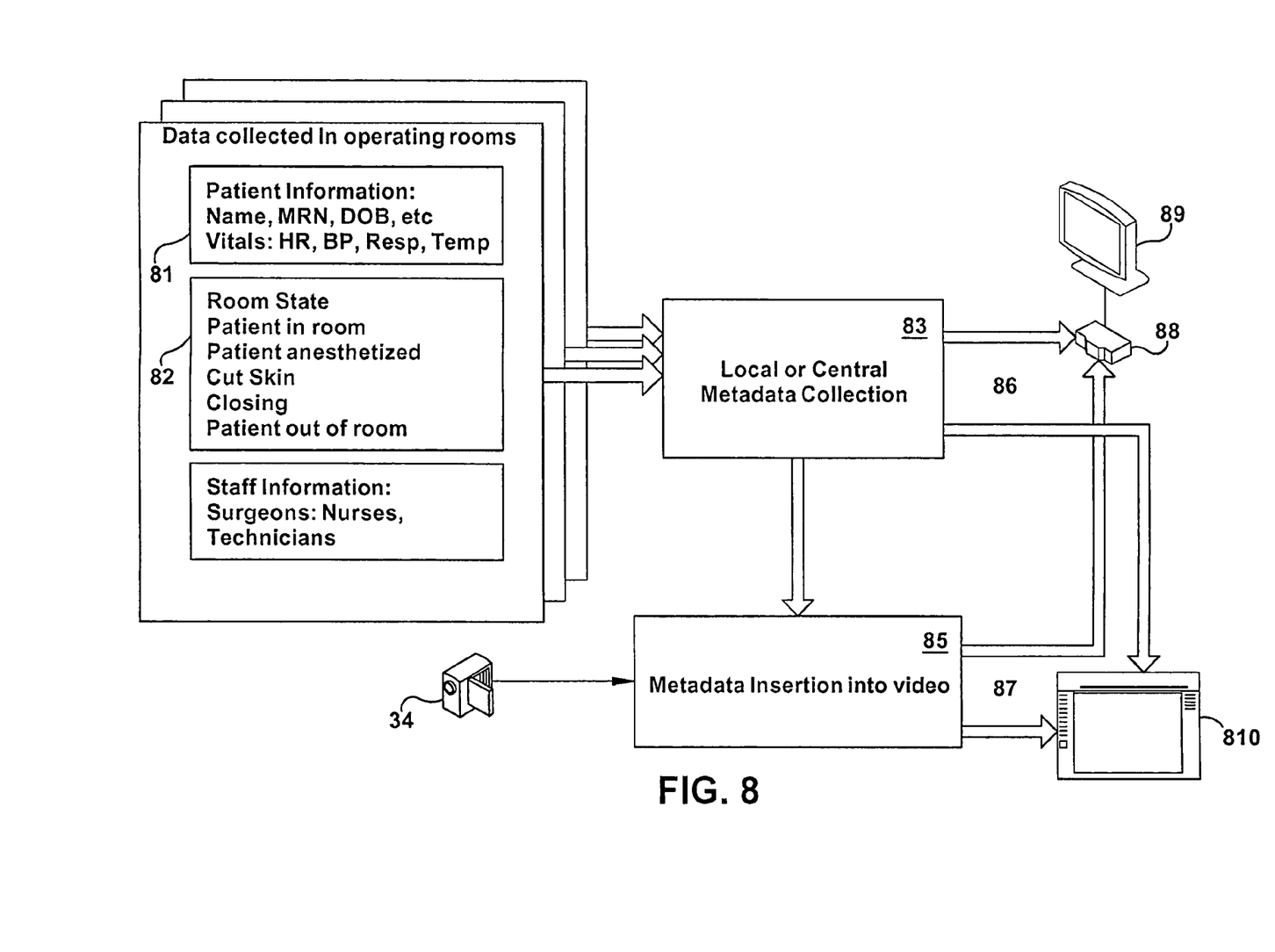
FIG. 8 is a diagram which describes the addition of metadata delivery and display to the digital video streaming system

Since digital video streams are being employed between the operating room and the plurality of viewing locations (ORs, Offices, Conference rooms), we are able to enrich the information that is being sent, by adding digital metadata content. There are many types of metadata that can be collected. There are many ways that the data can be collected and distributed. FIG. 8 is a diagram of two representative ways that metadata can be distributed within the system, and two ways that it can be viewed. In the operating room or clinic (81), there are many sources of clinically relevant information (82) that can be harvested and distributed. Some examples of this information are: patient information (e.g. DOB, vitals), operating room state, and staff. This information is collected either locally or centrally by a network based software service (83).

The information is persisted to a data store for later use when case documentation is reviewed and edited. The information is also distributed in real-time, or near real-time via connections (86, 87) to information consumers. The consumers may subscribe to some or all of the available information in the data stream. Information may be received directly as a digital metadata stream by smart displays and video decoder devices (88, 89), where it is mixed with incoming digital video streams. Information may also be received by computers, which host web browsers and/or specialized software applications (810), which are able to receive and display the digital metadata stream.

Metadata may also be mixed with video at (85), either by directly overlaying text and graphics into the video, or by using the closed captioning features of the MPEG video encoding standard. This enriched video content may be viewed directly by consumers via displays (89) or applications/web browsers (810).

It is important to note that collection and distribution of state and status information is critically useful to the OR staff. Storage of this metadata state information in a synchronized fashion with the recorded audio and video is an added benefit that can be used to assist doctors and users with the review and editing of recorded video.

The system is a highly flexible and powerful digital communication and productivity tool for the hospital operating room and clinical environment. Use of digital video streaming video technology enables viewing, conferencing and communications from virtually anywhere a data network is available.

A plurality of communications scenarios may be addressed, such as: Unidirectional viewing from virtually any location (with or without audio), with the advantages of remote device control and video selection capability.

EXAMPLE 1

A user in one OR wishes to view video in another OR

EXAMPLE 2

A user in an office wishes to view video from an OR

EXAMPLE 3

A user or group in a conference room wish to view video from an OR.

Bidirectional viewing of video (with or without audio)

EXAMPLE 1

Users in two ORs wish to communicate between ORs, using bidirectional links.

EXAMPLE: 2

Users in an OR and a conference room wish to communicate between locations.

A variety of end-point encoder/decoder/viewer configurations are possible with this system. Examples include:

Computers may be used for encoding, decoding, and viewing.

Hardware encoder/decoder sets may be purchased from 3.sup.rd party manufacturers.

Cameras and microphones may be connected to encoder devices.

Digital cameras with streaming outputs may be used directly with the system.

Displays and speaker systems may be connected to decoder devices.

The described systems and methods thus provide streaming digital video, audio and metadata content from operating rooms to multiple remote locations, and remote access and control of video sources within operating rooms for remote real-time viewing of surgical activity and information in multiple operating rooms.

What is claimed is:

1. A streaming managed medical video network system for enabling access on a medical network to live video data captured from a plurality of locations, the system comprising:
at least one streaming device associated with at least one medical treatment location, the at least one streaming device configured to receive live video data from at least one of a plurality of sources located in the at least one medical treatment location and convert the data received from the at least one source of the plurality of sources into a network packet stream, wherein the at least one source of the plurality of sources comprises a medical video source that views a procedure, the procedure comprising one of a surgical procedure, a diagnostic procedure, and a therapeutic procedure, performed at the at least one medical treatment location;
a first medical video source that views a procedure that is performed at the medical treatment location, the first medical video source being one of the plurality of sources located in the at least one medical treatment location and that is used during the procedure in which medical personnel are present at the medical treatment location to provide a first network packet stream;
a second medical video source that views the procedure that is performed at the medical treatment location, the second medical video source being one of the plurality of sources located in the at least one medical treatment location and that is used during the procedure in which medical personnel are present at the medical treatment location to provide a second network packet stream;
a network switch in communication with the at least one streaming device to receive at least one of the first network packet stream and the second network packet stream;
a streaming video control server that authenticates at least one of a plurality of users to the managed streaming medical video network system and provides the network packet stream to the at least one user such that, once the at least one user has been authenticated to the managed streaming medical video network system, the at least one user can view the network packet stream;
a communication channel that is established by the streaming video control server to route the at least one of the first network packet stream and the second network packet stream;
wherein the at least one streaming device captures video and metadata information, by (a) tracking a status of the at least one medical treatment location to provide metadata information, the status comprising a room status or a patient status, and (b) transmitting the metadata information with the video and (c) displaying the metadata information simultaneously with the video as the video is being viewed by the at least one user at a remote location.

2. The video network system of claim 1 wherein the transmitted metadata includes one of patient vital signs information, date of birth of patient, patient anesthesia status, patient presence in an operating, cut skin status and closing.

3. The video network system of claim 1 further comprising a video wall and at least one decoder associated with the video wall and in communication with the network switch, the at least one decoder configured to receive and decode the at least one packet streams routed by the streaming video control server for display on the video wall.

4. The video network system of claim 1 wherein the at least one streaming device is selected from the group consisting of standalone video encoders, video encoding and streaming computers, digital streaming cameras, and camera processors.

5. The video network system of claim 1 wherein the streaming video control server is configured to provide for point-to-point bi-directional video communications.

6. A streaming managed medical video network system for enabling access on a medical network to live video data captured from a plurality of locations, the system comprising:
at least one streaming device associated with at least one medical treatment location, the at least one streaming device configured to receive live video data from at least one of a plurality of sources located in the at least one medical treatment location and convert the data received from the at least one source of the plurality of sources into a network packet stream, wherein the at least one source of the plurality of sources comprises a medical video source that views a procedure, the procedure comprising one of a surgical procedure, a diagnostic procedure, and a therapeutic procedure, performed at the at least one medical treatment location;
a first medical video source that views a procedure that is performed at the medical treatment location, the first medical video source being one of the plurality of sources located in the at least one medical treatment location and that is used during the procedure in which medical personnel are present at the medical treatment location to provide a first network packet stream;
a network switch in communication with the at least one streaming device to receive at least one of the first network packet stream;
a streaming video control server that authenticates at least one of a plurality of users to the managed streaming medical video network system and provides the network packet stream to the at least one user such that, once the at least one user has been authenticated to the managed streaming medical video network system, the at least one user can view the network packet stream; and
a communication channel that is established by the streaming video control server to route the first network packet stream from the at least one streaming device, via the network switch, to the at least one user for enabling access by the at least one user to the network packet stream;
wherein the at least one streaming device captures video and enables a privacy mode status by collecting information and transmitting the video with an indication of the privacy mode status overlaid onto the video at a display device of the user so the privacy mode status is simultaneously viewed with the video displayed by the display device of the user at a remote location.

7. The video network system of claim 6 further comprising a video wall and at least one decoder associated with the video wall and in communication with the network switch, the at least one decoder configured to receive and decode the at least one packet streams routed by the streaming video control server for display on the video wall.

8. The video network system of claim 7 wherein the privacy status of an operating room is displayed on the video wall.

9. The video network system of claim 7 wherein the streaming video control server is programmed with privacy controls which enable users to control flow of video data.

10. A streaming managed medical video network system for enabling access on a medical network to live video data captured from a plurality of locations, the system comprising:
at least one streaming device associated with at least one medical treatment location of the plurality of locations, wherein the at least one streaming device is configured to receive live video data from at least one of a plurality of sources located in the at least one medical treatment location and convert the data received from the at least one source of the plurality of sources into a network packet stream, wherein the at least one source of the plurality of sources comprises a medical video source that views a procedure, the procedure comprising one of a surgical procedure, a diagnostic procedure, and a therapeutic procedure, performed at the at least one medical treatment location, the at least one medical treatment location having a plurality of medical video sources therein, the plurality of medical video sources being used during the procedure in which medical personnel are present at the medical treatment location;
wherein the at least one streaming device captures video simultaneously with state and status metadata information, by collecting patient vital signs information from a network-based software service and transmitting patient vital signs information together with the video to the at least one user at a remote location;
a network switch in communication with the at least one streaming device; and
streaming video control server that:
(a) authenticates at least one of a plurality of users to the managed streaming medical video network system;
(b) establishes a communication channel, the communications channel being configured to route each network packet stream from the at least one streaming device, via the network switch, towards the at least one user for enabling access by the at least one user to the network packet stream;
(c) provides the network packet stream to the at least one user such that, once the at least one user has been authenticated to the system, the at least one user can view the network packet stream; and
(d) tracks a status of the medical treatment location during one of the surgical procedure, the diagnostic procedure and the therapeutic procedure, the status of the medical treatment location comprising one of a room status and a patient status.

11. The system of claim 10 wherein the transmitted metadata includes one of patient vital signs information, date of birth of patient, patient anesthesia status, patient presence in an operating, cut skin status and closing.

12. The system of claim 11 wherein the metadata is displayed separately from the video.

13. The system of claim 12 wherein the display uses closed captioning features of the MPEG video coding standard.

14. The video network system of claim 1 wherein the metadata information comprises an indication of a privacy mode status that is transmitted to the at least one user at the remote location.

15. The video network system of claim 6 wherein the network-based software service comprises software or an application running on the streaming video control server.

16. The video network system of claim 6 wherein the network-based software service comprises software or an application that resides on a computer of the at least one user at the remote location.

17. The video network system of claim 6 wherein the privacy mode status is enabled by a local user at the at least one medical treatment location.

18. The video network system of claim 6 wherein the privacy mode status is overlaid onto the video as the video is being viewed by the at least one user at the remote location.

19. The video network system of claim 6 wherein the streaming video control server is programmed with privacy controls which enable users to control flow of video data.

20. A streaming managed medical video network system for enabling access on a medical network to live video data captured from a plurality of locations, the system comprising:

at least one streaming device associated with at least one medical treatment location, the at least one streaming device configured to receive live video data from at least one of a plurality of sources located in the at least one medical treatment location and convert the data received from the at least one source of the plurality of sources into a network packet stream, wherein the at least one source of the plurality of sources comprises a medical video source that views a procedure, the procedure comprising one of a surgical procedure, a diagnostic procedure, and a therapeutic procedure, performed at the at least one medical treatment location;

a first medical video source that views a procedure that is performed at the medical treatment location, the first medical video source being one of the plurality of sources located in the at least one medical treatment location and that is used during the procedure in which medical personnel are present at the medical treatment location to provide a first network packet stream;

a network switch in communication with the at least one streaming device to receive at least one of the first network packet stream;

a streaming video control server that authenticates at least one of a plurality of users to the managed streaming medical video network system and provides the network packet stream to the at least one user such that, once the at least one user has been authenticated to the managed streaming medical video network system, the at least one user can view the network packet stream; and a communication channel that is established by the streaming video control server to route the first network packet stream from the at least one streaming device, via the network switch, to the at least one user for enabling access by the at least one user to the network packet stream;

wherein the at least one streaming device captures video and enables a privacy mode status by collecting information and transmitting the video with an indication of the privacy mode status overlaid onto the video displayed by the display device of the user so the privacy mode status is simultaneously viewed with the video displayed by the display device of the user at a remote location.

21. The system of claim 6, wherein the video output displayed by the display device of the user comprises the network packet stream.

22. The system of claim 20, wherein the video output displayed by the display device of the user comprises the network packet stream.

* * * * *